United States Patent [19]

Martin et al.

[11] 4,130,588

[45] Dec. 19, 1978

[54] PROCESS FOR PRODUCING METHYLENE DIANILINE

[75] Inventors: Alton E. Martin; Warren D. White; Samuel L. Smolik, all of Lake Jackson, Tex.

[73] Assignee: The Dow Chemical Company, Midland, Mich.

[21] Appl. No.: 764,671

[22] Filed: Feb. 2, 1977

[51] Int. Cl.$^2$ ............................................. C07C 85/26
[52] U.S. Cl. ................................................. 260/570 D
[58] Field of Search ..................................... 260/570 D

[56] References Cited

U.S. PATENT DOCUMENTS

| | | | |
|---|---|---|---|
| 3,478,099 | 11/1969 | Ross et al. ............................. | 260/570 |
| 3,576,875 | 4/1971 | Rohe ...................................... | 260/570 |
| 3,952,042 | 4/1976 | Knofel ................................... | 260/570 X |
| 3,996,283 | 12/1976 | Knofel ................................... | 260/570 |

OTHER PUBLICATIONS

McCoy et al., "Chemistry and Industry", Apr. 18, 1970, pp. 531-532.

Primary Examiner—Robert V. Hines
Attorney, Agent, or Firm—J. G. Carter

[57] ABSTRACT

A process for producing polyamines such as methylene dianiline wherein an aromatic amine such as aniline is reacted with formaldehyde in the presence of an acid catalyst sufficient water is employed to cause a separation into an aqueous phase and an organic phase and the methylene dianiline is extracted with a solvent said process is improved by employing as the solvent a mixture of aniline and either a water immiscible organic solvent such as orthodichlorobenzene or conducting the extraction in the presence of a water soluble inorganic salt such as zinc nitrate or a combination thereof.

10 Claims, 3 Drawing Figures

PROCESS FOR PRODUCING METHYLENE DIANILINE

BACKGROUND OF THE INVENTION

This invention relates to a process for the preparation of polyamines and more particularly it relates to a process for separating the polyamine from the reactor effluent.

The preparation of polyamines such as methylene dianiline is well known and adequately described in U.S. Pat. No. 3,367,969, British Pat. Nos. 1,384,989 and 1,404,680.

British Pat. No. 1,384,989 discloses a process wherein the reaction mixture either contains or is made to contain a sufficient quantity of water to cause phase separation and a sufficiently quantity of aniline to convert the acid catalyst into its amine salt. The aqueous phase is then recycled to the reactor and the organic phase is then distilled to recover the product methylene dianiline.

British Pat. No. 1,404,680 discloses extracting the aqeuous condensation mixture with a water immiscible solvent and thereafter recovering the product from the organic phase by known methods and returning the aqueous phase to the beginning of the reaction cycle. The temperature employed during extraction was stated to be room temperature or higher preferably 70° C.-100° C. It is also stated that multi-stage extraction can be employed using pure solvent in the last stage and that 0-600% by weight of the starting amine can be employed after condensation.

U.S. Pat. No. 3,952,042 discloses extraction with a hydrophobic (water-immiscible) solvent which contains aniline at a temperature above 60° C. at a volume ratio of aqueous reactor effluent solution to aniline-containing solvent of 0.2:1 to 5:1. Also disclosed is extraction in a second stage wherein the aniline content of the hydrophobic solvent is less than in the first stage. In the first stage, the hydrophobic solvent contains 10–80% aniline and in the second stage it contains less than 10% aniline.

Some disadvantages in the above processes which can be overcome by the present invention include one or more of the following: loss of acid catalyst in the organic phase, loss of polyarylalkylene polyamine product which is recycled back to the reactor for further reaction into higher ring compounds, costly use of caustic for neutralization which results in a salt water pollution problem, increased energy cost with higher extraction temperatures. Another disadvantage which can be overcome by the process of the present invention is the inversion of phases in the extraction process when certain acid catalysts, for example methane sulfonic acid, are employed. This phase inversion prevents the use of continuous tower type extractors, which is the preferred means of performing this operation.

SUMMARY OF THE INVENTION

The present invention is therefore directed to a process for the preparation of polyamines such as methylene dianiline whereby an aryl amine such as aniline is reacted with formaldehyde in the presence of an acid catalyst such as methane sulfonic acid and sufficient water is employed to cause separation during extraction with the starting aryl amine into an organic phase and an aqueous phase and subsequently returning the aqueous phase which is essentially free of the polyamine product to the reactor, the improvement which comprises conducting the extraction at a temperature of from about 10° C. to about 50° C., preferably from about 20° C. to about 35° C. and either (1) employing with the aniline a water immiscible solvent in quantities from about 0% to about 15% and preferably from about 5% to about 10% by weight based upon the combined weight of aryl amine and water immiscible solvent;

(2) conducting the extraction in the presence of a water soluble inorganic salt which is non-reactive with any of the components of the process in quantities of from about 0% to about 25%, preferably from about 1% to about 10% by weight based upon the feed stream from the reactor to the extractor, or (3) a combination of (1) and (2); provided that when the quantity of water immiscible solvent is zero then the quantity of inorganic salt is at least 1% and that when the quantity of inorganic salt is zero, the quantity of water immiscible solvent is at least 5%.

The present invention is also directed to a process for the preparation of polyamines wherein an aryl amine is reacted with formaldehyde in the presence of an acid catalyst to form said polyamine, sufficient water is employed to cause separation of the reactant mixture during extraction of said mixture with the starting aryl amine into an organic phase and an aqueous phase and subsequently returning the aqueous phase to the reactor and recovering the resultant polyamine from the organic phase by known means, the improvement which comprises conducting the extraction in a single unit multi-stage extraction vessel at a temperature of from about 10° C. to about 50° C. employing a dual solvent system wherein one solvent is the aryl amine and the other is water, and either (1) employing with the aryl amine, a water immiscible solvent in quantities of from about 0% to about 50% preferably 5% to about 35% by weight based upon the combined weight of aryl amine and water immiscible solvent; or (2) conducting the extraction in the presence of a water soluble inorganic salt which is non-reactive with any of the components of the process in quantities of from about 0% to about 25% preferably from about 1% to about 15% by weight based upon the feed stream from the reactor to the extractor; or (3) a combination of (1) and (2); provided that when the quantity of water immiscible solvent is zero then the quantity of inorganic salt is at least 1% and that when the quantity of inorganic salt is zero, then the quantity of water immiscible solvent is at least 5%.

DETAILED DESCRIPTION OF THE INVENTION

In practicing the present invention the known aromatic amine to formaldehyde ratios of from about 1:1 to about 12:1 preferably from about 1.5:1 to about 8:1 are employed in the reaction. The formaldehyde is usually employed as an aqueous solution containing from about 30% to about 40% by weight of formaldehyde and a sufficient quantity of water should be present in the reactor to maintain total solvation of the reaction product.

Suitable aryl amines which can be employed in the present invention include, for example, aniline, 2,6-dimethyl aniline, 2,4-dimethyl aniline, 2,6-diisopropyl aniline, 2,4-diaminotoluene, o-toluidine, m-toluidine, N-methylaniline, N-ethylaniline, mixtures thereof and the like.

Suitable acid catalysts which can be employed in the preparation of methylene dianiline include those having a pKa value below 2.5 such as, for example, hydrochloric acid, hydrobromic acid, sulfuric acid, trifluoroacetic acid, methane sulfonic acid, trifluoromethanesulfonic acid, benzene sulfonic acid, phosphoric acid and the like.

Suitable water immiscible organic solvents which can be employed include, for example, chlorobenzene, dichlorobenzenes, trichlorobenzene, benzene, toluene, xylenes, dichloroethane, chloroform, carbon tetrachloride and the like.

Suitable water soluble inorganic salts which can be employed in the process of the present invention include, for example, sodium chloride, sodium nitrate, zinc sulfate, zinc nitrate, potassium nitrate, cadmium sulfate, calcium nitrate, mixtures thereof and the like.

Figure 1:
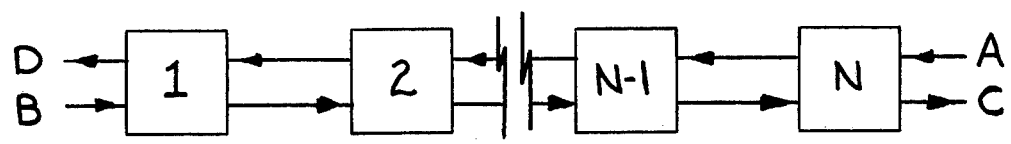
FIG. 1 is a flow diagram of a multistage multi-unit counter-current extraction process of N stages employing a single solvent system. The reactor effluent containing sufficient water to cause a phase separation and which may contain an inorganic salt is added at point A and the aqueous phase is removed at point D. The starting amine which may contain the water immiscible solvent is added at point B. The organic phase containing the product methylene dianiline is removed at point C. This flow diagram is for a system wherein the density of the aqueous phase is lighter than that of the organic phase. For those systems wherein the organic phase is lighter than the aqueous phase, then the points of introduction and removal are reversed.
Figure 2:
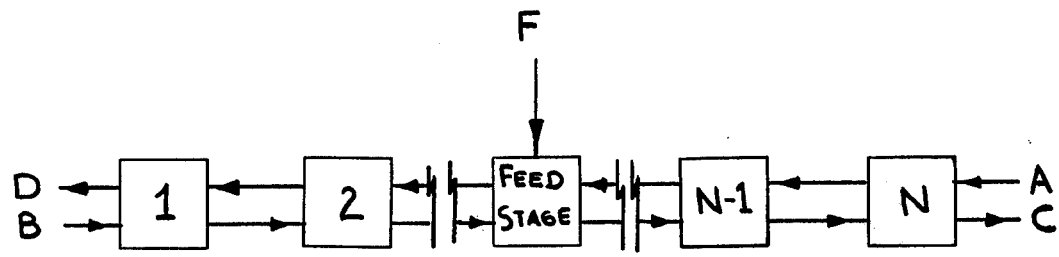
FIG. 2 is a flow diagram of a multistage, multi-unit, counter-current extraction process of N stages employing a two-solvent system. The starting amine which may contain the water immiscible solvent is introduced at point B. The organic phase containing the methylene dianiline product is removed at point C. The water employed as a water wash, is introduced at point A and the aqueous phase is removed at point D. The reactor effluent which may contain the inorganic salt is introduced into the feed stage at point F. As in FIG. 1, if the organic phase is lighter than the aqueous phase, then the points of introduction and removal are reversed.
Figure 3:
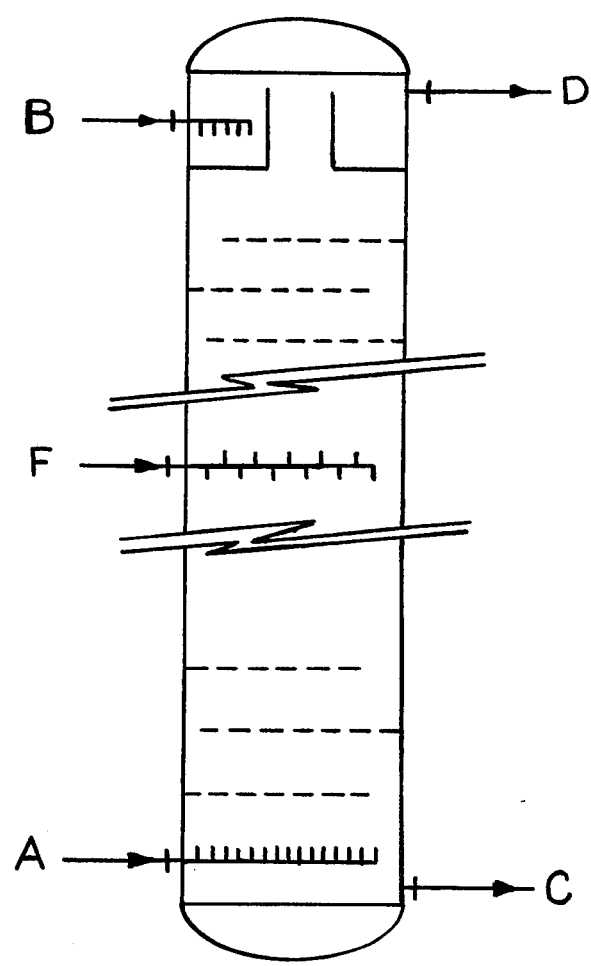
FIG. 3 is a flow diagram of a multi-stage, single unit extraction vessel wherein the number of stages is designed into the unit and depends upon the type of packing or trays in the column as well as the height of the packing or the number of trays. The definitions of points A, B, C, D and F are the same as for FIG. 2 as well as the discussion concerning the densities of the aqueous and organic phases. A column of this type is the preferred means of operating this process. The dotted lines represent trays or theoretical stages of the packing.

In the most desirable embodiment of the invention a two-solvent extraction process is employed with water as the one solvent and the starting aryl amine as the other. The aryl amine may contain an organic water immiscible solvent as previously described and/or the reactor effluent may contain a water soluble inorganic salt. There must be sufficient arylamine introduced to the extraction system to convert the entire amount of acid catalyst present into its arylamine salts and to also extract the polyamine product. The column illustrated by FIG. 3 can be employed to accomplish this on a commercial scale by maintaining the concentrations of the water immiscible solvent and/or the water soluble inorganic salt such that the density of the organic phase is consistently higher or lower than that of the aqueous phase.

The organic phase which contains the polyamine can be treated in a known manner such as distillation to recover the polyamine product and solvents and arylamine which can be recycled to various parts of the process in a known manner.

Also, it may be desirable to remove some of the water from the aqueous phase before recycling it to the reactor.

The following examples are illustrative of the invention but are not to be construed as limiting the scope thereof in any manner.

The following examples and comparative experiments were performed in separatory funnels which simulate multi-stage extraction as illustrated in *LIQUID-LIQUID EXTRACTION* by L. Alders, Elsevier Publishing Co., 1955, Chapters IV and V, particularly pp. 115–122, 136–137 and 172–173.

EXAMPLES 1–3 and COMPARATIVE EXPERIMENTS A–D

In each of the examples and comparative experiments, a counter-current extraction employing a 30-minute hold-up time per stage to insure equilibrium and operating at room temperature was employed. The number of theoretical stages, feed compositions, solvent composition, aqueous phase composition, and organic phase composition for each example and comparative experiment are given in Table I.

MDA = methylene dianiline
MSA = methane sulfonic acid
ODCB = orthodichlorobenzene (water immiscible solvent)

TABLE I

|  | Comparative Experiment A | Example 1 | Example 2 | Comparative Experiment B |
|---|---|---|---|---|
| Feed[5] |  |  |  |  |
| MDA, g | 14.2 | 14.2 | 14.2 | 14.2 |
| MSA, g | 14.2 | 14.2 | 14.2 | 14.2 |
| Water, g | 80.8 | 80.8 | 80.8 | 80.8 |
| $Zn(NO_3)_2$, g/%[4] | 0 | 0 | 0 | 0 |
| Solvent |  |  |  |  |
| Aniline, g | 41 | 41 | 41 | 41 |
| ODCB, g/%[1] | 0/0 | 2.2/5.09 | 4.6/10.9 | 20.2/33.01 |
| Aqueous Phase[6] |  |  |  |  |
| MDA, g/%[2] | 0.09/0.63 | 0.11/0.66 | 0.14/0.99 | 0.59/4.15 |
| MSA, g/%[3] | 6.58/46.34 | 8.31/58.52 | 8.41/59.23 | 2.79/90.07 |
| Organic Phase[7] |  |  |  |  |
| MDA, g/%[2] | 14.03/98.8 | 14.09/99.23 | 14.02/98.73 | 3.61/95.85 |
| MSA, g/%[3] | 7.55/53.16 | 5.89/41.48 | 5.79/40.77 | 1.41/9.93 |
| Number of Stages | 4 | 4 | 4 | 4 |

TABLE I-continued

|  | Comparative Experiment C | Comparative Experiment D | Example 3 | Comparative Experiment E |
|---|---|---|---|---|
| Feed[5] | | | | |
| MDA, g | 14.2 | 14.2 | 13.14 | 13.14 |
| MSA, g | 14.2 | 14.2 | 13.14 | 13.14 |
| Water, g | 80.8 | 80.8 | 76.65 | 76.65 |
| $Z_n(NO_3)_2$, g/%[4] | 0 | 0 | 6.57/6.0 | 0 |
| Solvent | | | | |
| Aniline, g | 41 | 41 | 61 | 61 |
| ODCB, g/%[1] | 61.5/60 | 164/80 | 0 | 0 |
| Aqueous Phase[6] | | | | |
| MDA, g/%[2] | 1.95/13.75 | 3.46/24.37 | 0.13/0.99 | 0.81/6.16 |
| MSA, g/%[3] | 14.04/98.87 | 14.2/100 | 7.97/60.65 | 7.85/59.72 |
| Organic Phase[7] | | | | |
| MDA, g/%[2] | 12.55/88.38 | 10.74/75.64 | 13.01/99.01 | 12.33/93.84 |
| MSA, g/%[3] | 0.16/1.13 | 0/0 | 5.17/39.35 | 5.29/40.28 |
| Number of Stages | 4 | 4 | 2 | 2 |

[1] as % of aniline + ODCB
[2] as % of total MDA in feed
[3] as % of total MSA in feed
[4] as % of feed
[5] the MDA and MSA are in the form of a salt
[6] the MDA is present in salt form with MSA. The remaining portion of MSA is present in salt form with aniline.
[7] the MDA is present as free amine. The MSA is present in salt form.

As can be seen from Examples 1–2 and Comparative Experiments A–D, most of the MDA, 98.73 to 99.23% is extracted in the organic phase while less catalyst is carried over into the organic phase than is carried over when no ODCB was employed, e.g. 41.48% as compared to 53.17%. At the higher levels of ODCB less of the catalyst is retained in the organic phase, but more product MDA is retained in the aqueous phase to be returned to the reactor which is undesirable in that MDA can react with formaldehyde to form higher polyamines.

Example 3 shows that more of the total MDA is extracted (99.01%) by the presence of a water soluble inorganic salt as compared to Comparative Experiment E in which only 93.84% was extracted.

EXAMPLE 4 AND COMPARATIVE EXPERIMENT F

The example and comparative experiment were conducted in the same manner as the previous examples and comparative experiments except that a dual solvent system was employed. The dual extraction system employed an organic solvent consisting of aniline and ODCB, and an aqueous solvent which was water. The feed was introduced at the 4th stage counted from the water feed point or at the 6th stage counted from the organic solvent feed point.

The number of stages, feed compositions, solvent compositions, aqueous phase composition, and organic phase composition for each of these examples and comparative experiment are given in Table II.

TABLE II

|  | Example 4 | Comparative Experiment F |
|---|---|---|
| Feed[4] | | |
| MDA, g | 14.2 | 14.2 |
| MSA, g | 14.2 | 14.2 |
| Water, g | 40.1 | 40.1 |
| Organic Solvent | | |
| Aniline, g | 41 | 41 |
| ODCB, g/%[1] | 4.56/10 | 20.2/33 |
| Aqueous Solvent | | |
| Water, g | 41 | 41 |
| Aqueous Phase[5] | | |
| MDA, g/%[2] | 0.1/0.7 | 0.18/1.27 |
| MSA, g/%[3] | 14.2/100 | 14.2/100 |
| Organic Phase[6] | | |
| MDA, g/%[2] | 14.1/99.3 | 14.02/98.73 |
| MSA, g/%[3] | 0/0 | 0/0 |
| Number of Stages | 9 | 9 |

[1] as % of aniline + ODCB
[2] as % of total MDA in feed
[3] as % of total MSA in feed
[4] the MDA and MSA are in the form of a salt
[5] the MDA is present in salt form with MSA. The remaining portion of MSA is present in salt form with aniline.
[6] the MDA is present as free amine. The MSA is present in salt form.

As can be seen in the Example 4 and Comparative Experiment F, the use of a dual solvent system, i.e., organic and aqueous results in no catalyst being retained in the organic phase and that when the higher quantity of ODCB is employed, more product MDA is retained in the aqueous phase to be returned to the reactor which is undesirable in that MDA can react with the reaction mixture to form higher polyamines.

We claim:

1. In a process for the preparation of polyamines wherein an aryl amine is reacted with formaldehyde in the presence of an acid catalyst to form said polyamine, sufficient water is employed to cause separation of the reactant mixture during extraction of said mixture with the aryl amine into an organic phase and an aqueous phase and subsequently returning the aqueous phase to the reactor and recovering the resultant polyamine from the organic phase by known means, the improvement which comprises conducting the extraction at a temperature of from about 10° C. to about 50° C. and
   conducting the extraction in the presence of a water soluble inorganic salt which is non-reactive with any of the components of the process in quantities of from about 1% to about 25% by weight based upon the feed stream from the reactor to the extractor.

2. The process of claim 1 wherein the aryl amine is aniline and the polyamine is methylene dianiline and the acid catalyst is methane sulfonic acid.

3. The process of claim 2 wherein the extraction is conducted at a temperature of from about 20° to about 35° C.

4. The process of claim 3 wherein a water soluble inorganic salt is employed in quantities of from about 1% to about 10%.

5. The process of claim 4 wherein the water soluble inorganic salt is zinc nitrate.

6. In a process for the preparation of polyamines wherein an aryl amine is reacted with formaldehyde in the presence of an acid catalyst to form said polyamine sufficient water is employed to cause separation of the reactant mixture during extraction of said mixture with the aryl amine into an organic phase and an aqueous phase and subsequently returning the aqueous phase to the reactor and recovering the resultant polyamine from the organic phase by known means, the improvement which comprises conducting the extraction in a single unit multi-stage extraction vessel at a temperature of from about 10° C. to about 50° C. employing a dual solvent system wherein one solvent is the aryl amine and the other is water, and conducting the extraction in the presence of a water soluble inorganic salt which is non-reactive with any of the components of the process in quantities of from about 1% to about 25% by weight based upon the feed stream from the reactor to the extractor.

7. The process of claim 6 wherein the aryl amine is aniline and the polyamine is methylene dianiline and the acid catalyst is methane sulfonic acid.

8. The process of claim 7 wherein the extraction is conducted at a temperature of from about 20° to about 35° C.

9. The process of claim 8 wherein a water soluble inorganic salt is employed in quantities of from about 1% to about 15%.

10. The process of claim 9 wherein the water soluble inorganic salt is zinc nitrate.

* * * * *